(12) United States Patent
Wright et al.

(10) Patent No.: US 9,433,721 B2
(45) Date of Patent: Sep. 6, 2016

(54) VIAL SPIKING ASSEMBLIES AND RELATED METHODS

(71) Applicant: Fresenius Medical Care Holdings, Inc., Waltham, MA (US)

(72) Inventors: Nigel Wright, California, PA (US); Michael John Zang, Allison Park, PA (US); Tom Monahan, Wexford, PA (US); John A. Barron, Seven Fields, PA (US); Douglas Mark Zatezalo, Allison Park, PA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 375 days.

(21) Appl. No.: 13/926,500

(22) Filed: Jun. 25, 2013

(65) Prior Publication Data
US 2014/0374353 A1    Dec. 25, 2014

(51) Int. Cl.
*A61M 1/36* (2006.01)
*A61M 1/34* (2006.01)
*A61M 5/145* (2006.01)
*A61M 5/14* (2006.01)

(52) U.S. Cl.
CPC ............ *A61M 1/3644* (2014.02); *A61M 1/342* (2013.01); *A61M 1/3643* (2013.01); *A61M 5/145* (2013.01); *A61M 2005/1402* (2013.01); *A61M 2205/584* (2013.01); *A61M 2205/60* (2013.01)

(58) Field of Classification Search
USPC .......................... 210/188, 198.1, 646, 85, 95
See application file for complete search history.

(56) References Cited

U.S. PATENT DOCUMENTS

| | | |
|---|---|---|
| 3,946,731 A | 3/1976 | Lichtenstein |
| 3,982,538 A | 9/1976 | Sharpe |
| 3,985,135 A | 10/1976 | Carpenter et al. |
| 3,996,027 A | 12/1976 | Schnell et al. |
| 4,014,206 A | 3/1977 | Taylor |
| 4,026,669 A | 5/1977 | Leonard et al. |
| 4,137,160 A | 1/1979 | Ebling et al. |
| 4,187,057 A | 2/1980 | Xanthopoulos |
| 4,231,370 A | 11/1980 | Mroz et al. |

(Continued)

FOREIGN PATENT DOCUMENTS

| | | |
|---|---|---|
| DE | 4240681 | 6/1994 |
| DE | 102005001779 | 9/2006 |

(Continued)

OTHER PUBLICATIONS

Notification of Transmittal of the International Search Report and the Written Opinion of the International Searching Authority for corresponding PCT Application No. PCT/US2014/043565, mailed Oct. 22, 2014, 13 pages.

(Continued)

*Primary Examiner* — Dirk Bass
(74) *Attorney, Agent, or Firm* — Fish & Richardson P.C.

(57) ABSTRACT

This disclosure relates to vial spiking assemblies and related methods. In certain aspects, the vial spiking assemblies include a vial adapter having a base, a spike extending from a central region of the base, and a sidewall extending from the base and surrounding the spike. The base and the sidewalls partially, define a cavity that is configured to receive at least a portion of the vial. The assemblies also include a spike cover that is removably attached to the spike and that includes a material configured to indicate when the material is contacted with liquid.

24 Claims, 9 Drawing Sheets

(56) References Cited

U.S. PATENT DOCUMENTS

| | | |
|---|---|---|
| 4,370,983 A | 2/1983 | Lichtenstein |
| 4,459,139 A | 7/1984 | von Reis et al. |
| 4,488,961 A | 12/1984 | Spencer |
| 4,530,759 A | 7/1985 | Schal |
| 4,572,724 A | 2/1986 | Rosenberg et al. |
| 4,590,227 A | 5/1986 | Nakamura et al. |
| 4,643,713 A | 2/1987 | Viitala |
| 4,662,906 A | 5/1987 | Matkovich et al. |
| 4,695,385 A | 9/1987 | Boag |
| 4,702,675 A | 10/1987 | Aldrovandi et al. |
| 4,702,829 A | 10/1987 | Polaschegg et al. |
| 4,888,004 A | 12/1989 | Williamson et al. |
| 4,898,576 A | 2/1990 | Philip |
| 4,997,464 A | 3/1991 | Kopf |
| 5,061,236 A | 10/1991 | Sutherland et al. |
| 5,330,425 A | 7/1994 | Utterberg |
| 5,425,173 A | 6/1995 | Moss et al. |
| 5,438,510 A | 8/1995 | Bryant et al. |
| 5,441,636 A | 8/1995 | Chevallet et al. |
| 5,460,490 A | 10/1995 | Carr et al. |
| 5,498,338 A | 3/1996 | Kruger et al. |
| 5,540,265 A | 7/1996 | Polaschegg et al. |
| 5,578,070 A | 11/1996 | Utterberg |
| 5,591,344 A | 1/1997 | Kenley et al. |
| 5,614,677 A | 3/1997 | Wamsiedler et al. |
| 5,628,908 A | 5/1997 | Kamen et al. |
| 5,643,205 A | 7/1997 | Utterberg |
| 5,651,893 A | 7/1997 | Kenley et al. |
| 5,674,390 A | 10/1997 | Matthews et al. |
| 5,674,404 A | 10/1997 | Kenley et al. |
| 5,690,831 A | 11/1997 | Kenley et al. |
| 5,693,008 A | 12/1997 | Brugger et al. |
| 5,711,883 A | 1/1998 | Folden et al. |
| 5,714,060 A | 2/1998 | Kenley et al. |
| 5,725,776 A | 3/1998 | Kenley et al. |
| 5,788,671 A | 8/1998 | Johnson |
| 5,849,065 A | 12/1998 | Wojke |
| 5,863,421 A | 1/1999 | Peter et al. |
| 5,928,177 A | 7/1999 | Brugger et al. |
| 5,938,634 A | 8/1999 | Packard |
| 5,989,423 A | 11/1999 | Kamen et al. |
| 6,179,801 B1 | 1/2001 | Holmes et al. |
| 6,196,987 B1 | 3/2001 | Holmes et al. |
| 6,200,287 B1 | 3/2001 | Keller et al. |
| 6,210,591 B1 | 4/2001 | Krivitski |
| 6,231,537 B1 | 5/2001 | Holmes et al. |
| 6,234,989 B1 | 5/2001 | Brierton et al. |
| 6,280,406 B1 | 8/2001 | Dolecek et al. |
| 6,299,583 B1 | 10/2001 | Eggers et al. |
| 6,336,916 B1 | 1/2002 | Bormann et al. |
| 6,337,049 B1 | 1/2002 | Tamari |
| 6,361,518 B1 | 3/2002 | Brierton et al. |
| 6,383,158 B1 | 5/2002 | Utterberg et al. |
| 6,406,631 B1 | 6/2002 | Collins et al. |
| 6,409,696 B1 | 6/2002 | Toavs et al. |
| 6,497,674 B1 | 12/2002 | Steele et al. |
| 6,497,676 B1 | 12/2002 | Childers et al. |
| 6,503,062 B1 | 1/2003 | Gray et al. |
| 6,514,225 B1 | 2/2003 | Utterberg et al. |
| 6,536,278 B1 | 3/2003 | Scagliarini |
| 6,695,803 B1 | 2/2004 | Robinson et al. |
| 6,725,726 B1 | 4/2004 | Adolfs et al. |
| 6,730,055 B2 | 5/2004 | Bainbridge et al. |
| 6,730,233 B2 | 5/2004 | Pedrazzi |
| 6,743,201 B1 | 6/2004 | Dönig et al. |
| 6,755,801 B2 | 6/2004 | Utterberg et al. |
| 6,764,460 B2 | 7/2004 | Dolecek et al. |
| 6,790,195 B2 | 9/2004 | Steele et al. |
| 6,814,864 B1 | 11/2004 | Favre et al. |
| 6,821,441 B2 | 11/2004 | Pedrini et al. |
| 6,852,090 B2 | 2/2005 | Burbank et al. |
| 6,887,214 B1 | 5/2005 | Levin et al. |
| 6,973,373 B2 | 12/2005 | Gray et al. |
| 6,979,309 B2 | 12/2005 | Burbank et al. |
| 7,021,148 B2 | 4/2006 | Kuhn et al. |
| 7,083,719 B2 | 8/2006 | Bowman et al. |
| 7,115,107 B2 | 10/2006 | Delnevo et al. |
| 7,238,164 B2 | 7/2007 | Childers et al. |
| 7,255,680 B1 | 8/2007 | Gharib |
| 7,273,465 B2 | 9/2007 | Ash |
| 7,476,209 B2 | 1/2009 | Gara et al. |
| 7,517,387 B2 | 4/2009 | Chevallet et al. |
| 7,603,907 B2 | 10/2009 | Reiter et al. |
| 7,621,983 B2 | 11/2009 | Neri |
| 7,766,873 B2 | 8/2010 | Moberg et al. |
| 7,871,391 B2 | 1/2011 | Folden et al. |
| 7,892,331 B2 | 2/2011 | Childers et al. |
| 7,892,332 B2 | 2/2011 | Prisco et al. |
| 7,905,853 B2 | 3/2011 | Chapman et al. |
| 8,110,104 B2 | 2/2012 | Crnkovich et al. |
| 8,858,487 B2 | 10/2014 | Suzuki |
| 2001/0021817 A1 | 9/2001 | Brugger et al. |
| 2002/0014462 A1 | 2/2002 | Muller |
| 2002/0072718 A1 | 6/2002 | Brugger et al. |
| 2002/0179527 A1 | 12/2002 | Yao |
| 2004/0019312 A1 | 1/2004 | Childers et al. |
| 2004/0154967 A1 | 8/2004 | Pedrazzi |
| 2004/0238416 A1 | 12/2004 | Burbank et al. |
| 2005/0054968 A1 | 3/2005 | Giannella |
| 2005/0126998 A1 | 6/2005 | Childers |
| 2005/0131332 A1 | 6/2005 | Kelly et al. |
| 2005/0132826 A1 | 6/2005 | Teugels |
| 2005/0230292 A1 | 10/2005 | Beden et al. |
| 2005/0251086 A1 | 11/2005 | Sternby |
| 2005/0274658 A1 | 12/2005 | Rosenbaum et al. |
| 2007/0078369 A1 | 4/2007 | Tamari |
| 2007/0086924 A1 | 4/2007 | Moses |
| 2007/0106198 A1 | 5/2007 | Folden et al. |
| 2007/0112297 A1 | 5/2007 | Plahey et al. |
| 2007/0158247 A1 | 7/2007 | Carr et al. |
| 2007/0158268 A1 | 7/2007 | DeComo |
| 2007/0193940 A1 | 8/2007 | Duchamp et al. |
| 2007/0269340 A1 | 11/2007 | Dannenmaier et al. |
| 2008/0149563 A1 | 6/2008 | Ash |
| 2008/0177216 A1 | 7/2008 | Ash |
| 2008/0208011 A1 | 8/2008 | Shuler |
| 2008/0275364 A1 | 11/2008 | Conway et al. |
| 2009/0012442 A9 | 1/2009 | Brugger et al. |
| 2009/0012449 A1 | 1/2009 | Lee et al. |
| 2009/0071911 A1 | 3/2009 | Folden et al. |
| 2009/0084721 A1 | 4/2009 | Yardimci et al. |
| 2009/0101576 A1 | 4/2009 | Rohde et al. |
| 2009/0216211 A1 | 8/2009 | Beden et al. |
| 2009/0320684 A1 | 12/2009 | Weaver et al. |
| 2010/0004589 A1 | 1/2010 | Hedmann et al. |
| 2010/0063445 A1 | 3/2010 | Sternberg et al. |
| 2010/0133189 A1 | 6/2010 | Maierhofer et al. |
| 2010/0206784 A1 | 8/2010 | Weaver et al. |
| 2010/0222735 A1 | 9/2010 | Plahey et al. |
| 2010/0237011 A1 | 9/2010 | Ross et al. |
| 2010/0292627 A1 | 11/2010 | Caleffi et al. |
| 2011/0004143 A1 | 1/2011 | Beiriger |
| 2011/0120946 A1 | 5/2011 | Levin et al. |

FOREIGN PATENT DOCUMENTS

| | | |
|---|---|---|
| EP | 0235591 | 9/1987 |
| EP | 0327136 | 8/1989 |
| EP | 0458041 | 11/1991 |
| EP | 0728509 | 8/1996 |
| EP | 0887100 | 12/1998 |
| EP | 1529545 | 5/2005 |
| EP | 1547630 | 6/2005 |
| EP | 1728526 | 12/2006 |
| EP | 1894587 | 3/2008 |
| EP | 2226087 | 9/2010 |
| GB | 2424966 | 10/2006 |
| JP | 02289259 | 11/1990 |
| JP | 2002095741 | 4/2002 |
| JP | 2003180834 | 7/2003 |
| JP | 2005218709 | 8/2005 |
| JP | 2005530543 | 10/2005 |
| WO | 9650322 | 12/1996 |
| WO | 9702056 | 1/1997 |

(56) References Cited

FOREIGN PATENT DOCUMENTS

| WO | 0108722 | 2/2001 |
|---|---|---|
| WO | 0150949 | 7/2001 |
| WO | 0164312 | 9/2001 |
| WO | 0226286 | 4/2002 |
| WO | 2004000391 | 12/2003 |
| WO | 2005044340 | 5/2005 |
| WO | 2005044341 | 5/2005 |
| WO | 2005065745 | 7/2005 |
| WO | 2005077490 | 8/2005 |
| WO | 2007050211 | 5/2007 |
| WO | 2008002370 | 1/2008 |
| WO | WO2011002853 A2 | 1/2011 |

OTHER PUBLICATIONS

Gambro®, "DEHP-Free Cartridge Blood Sets", © Nov. 2004, Gambro, Inc, Lakewood, CO, 4 pp.

Gambro®, "Prisma® HF 1000, For Increased Filtration Capacity", © Aug. 2001, Gambro Renal Products, Inc., Lakewood, CO, 2 pp.

Gambro®, "Prisma® M60 and M100 Pre-Pump Infusion Sets—Introducing: The unique solution that enables Physicians to choose a predilution method that meets the needs of their patients", © 2004, Gambro Inc., Lakewood, CO, 4 pp.

Gambro®, "Prismaflex ™, Anticipating Critical Care needs and taking our innovative response . . . to new heights", © 2004, Gambro Inc., Lakewood, CO, 8 pp.

Manns et al., "The acu-men: A new device for continuous renal replacement therapy in acute renal failure," Kidney International, vol. 54, pp. 268-274, 1998.

Acu-men, Acute Dialysis Machine Operating Instructions, Software Version 1.0, Fresenius MY acu-men, Jan. 5, 1996 (OP), 146 pages.

Dietrich Polaschegg and Levin, Hemodialysis Machines and Monitors, Replacement of Renal Function by Dialysis, Fourth Edition, Chapter 14, pp. 334-379, 1996.

Dinesh Khullar, Basic Fundamentals of Dialysis, JIMSA, vol. 15, No. 3, pp. 163-169, Jul.-Sep. 2002.

Wamsiedler et al., Heparin-Free Dialysis with an On-Line Hemodiafiltration System, Artificial Organs, 17(11) pp. 948-953, Feb. 1993.

Operator's Manual for MeDSpump: a healthy dose of innovation, Fresenius Medical Care North America, 2008, 47 pages.

VIAL SPIKING ASSEMBLIES AND RELATED METHODS

TECHNICAL FIELD

This disclosure relates to vial spiking assemblies and related methods.

BACKGROUND

During hemodialysis, impurities and toxins are removed from the blood of a patient by drawing the blood out of the patient through a blood access site, typically via a catheter, and then passing the blood through an artificial kidney (often referred to as a "dialyzer"). The artificial kidney includes microtubes that each separate a first conduit from a second conduit. Generally, a dialysis solution (often referred to as a "dialysate") flows through the first conduit of the dialyzer while the patient's blood flows through the second conduits of the dialyzer, causing impurities and toxins to be transferred from the blood to the dialysate through the microtubes. The impurities and toxins can, for example, be removed from the blood by a diffusion process. After passing through the dialyzer, the purified blood is then returned to the patient.

When kidney failure is diagnosed, patients are typically given medication to help control the symptoms and slow the progress of damage to the kidneys. Patients with chronic kidney failure generally take drugs, such as iron supplements, to control the balance of minerals in the body.

SUMMARY

In one aspect, a vial spiking assembly includes a vial adapter that includes a base, a spike extending from a central region of the base, a sidewall extending from the base and substantially surrounding the spike in which the base and the side wall at least partially define a cavity configured to receive a portion of a vial, a spike cover removably attachable to the spike. The spike cover includes a material configured to indicate when the material has been contacted with liquid.

In another aspect, a method includes causing a priming fluid to flow through a drug delivery line of a dialysis system until the priming fluid contacts a material of a vial adapter assembly causing the material to indicate contact of the priming fluid with the vial adapter assembly and stopping the flow of priming fluid through the drug delivery line after the material indicates contact of the priming fluid with the vial adapter assembly.

In a further aspect, a dialysis system includes a dialysis machine including a blood pump and a drug pump, a blood line set including a blood line that can be operably connected to the blood pump and a drip chamber in fluid communication with the blood line, and a fluid line set including a fluid line that can be connected to the drip chamber of the blood line set and to a vial adapter. The vial adapter includes a base, a spike extending from a central region of the base, a sidewall extending from the base and substantially surrounding the spike in which the base and the side wall at least partially define a cavity configured to receive a portion of a vial, a spike cover removably attachable to the spike. The spike cover includes a material that is configured to indicate when the material has been contacted with liquid.

Implementations can include one or more of the following features.

In some implementations, the material is a color changing material that changes color when contacted by a liquid.

In certain implementations, the color changing material is a microporous material impregnated with at least one of the following: bromophenol blue, cobalt chloride, a food dye, powder dye, and a color additive.

In some implementations, the microporous material is molded with a color additive that changes color when contacted with liquid.

In certain implementations, the microporous material has an average pore size capable of permitting air to flow therethrough and preventing liquid from flowing therethrough.

In some implementations, the microporous material surrounds the spike when the spike cover is attached to the spike.

In certain implementations, the spike cover is movable away from the base from a first position wherein the cover at least partially covers a tip of the spike of the vial adapter to a second position wherein the tip of the vial adapter is fully exposed.

In some implementations, the spike cover includes a housing defining a cavity in which the material is disposed.

In certain implementations, the housing is formed of a gas permeable material.

In some implementations, the material is visible through the housing.

In certain implementations, the drug delivery line is connected to a vial adapter assembly comprising a vial adapter having a spike extending from a central region of a base, and a spike cover that can be removably attached to the spike.

In some implementations, the spike cover includes the material.

In certain implementations, the microporous material has an average pore size of about 5 to 45 microns.

In some implementations, causing the priming fluid to flow through the drug delivery line causes air in the drug delivery line to exit through the vial adapter assembly.

In certain implementations, the method further includes connecting the drug delivery line to a blood line set of the dialysis system before the priming fluid flows through the drug delivery line.

In some implementations, the drug delivery line is connected to a drip chamber of the blood line set.

In certain implementations, causing the priming fluid to flow through the drug delivery line includes causing the priming fluid to flow to the drip chamber and overfill the drip chamber, and the overfilling of the drip chamber forces the priming fluid through the drug delivery line.

In some implementations, causing the priming fluid to flow through the drug delivery line includes causing the priming fluid to flow from a priming fluid bag to the drip chamber, and from the drip chamber to a vial spiking assembly.

In some implementations, the method further includes removing the spike cover after stopping the flow of priming fluid, inserting a drug vial onto the vial adapter assembly, and initiating drug delivery.

In certain implementations, initiating drug delivery comprises operating a drug delivery pump to cause drug from the drug vial to mix with a patient's blood prior to delivery of the blood to the patient.

In some implementations, the drip chamber is downstream of the blood pump and the fluid line is connected to a top region of the drip chamber.

In certain implementations, the microporous material is covalently bonded with a color additive that changes color when contacted with liquid.

In some implementations, the microporous material has an average pore size capable of permitting air to flow through and preventing liquid from flowing through.

In certain implementations, the drip chamber is downstream of the blood plump.

In some implementations, the fluid line is connected to a top portion of the drip chamber.

Implementations can include one or more of the following advantages.

The vial spiking assemblies described herein are designed to be used in medical systems, such as hemodialysis systems. Priming the drug delivery line of such systems ensures that the already sterile drug delivery line set is fully filled with liquid, which blocks potential ingress points for pathogens. In addition, priming the drug delivery line set reduces the likelihood of air being delivered to the patient during treatment. These vial spiking assemblies improve the process of priming of the system by providing a clear and easily obtainable indication that the drug delivery line is fully primed. Further, by connecting the drug delivery line to the system, both the blood line set and the drug delivery line set can be primed using one pump (e.g., the blood pump) during priming.

Other aspects, features, and advantages of the disclosed subject matter will be apparent from the description and drawings, and from the claims.

DETAILED DESCRIPTION

Figure 1:
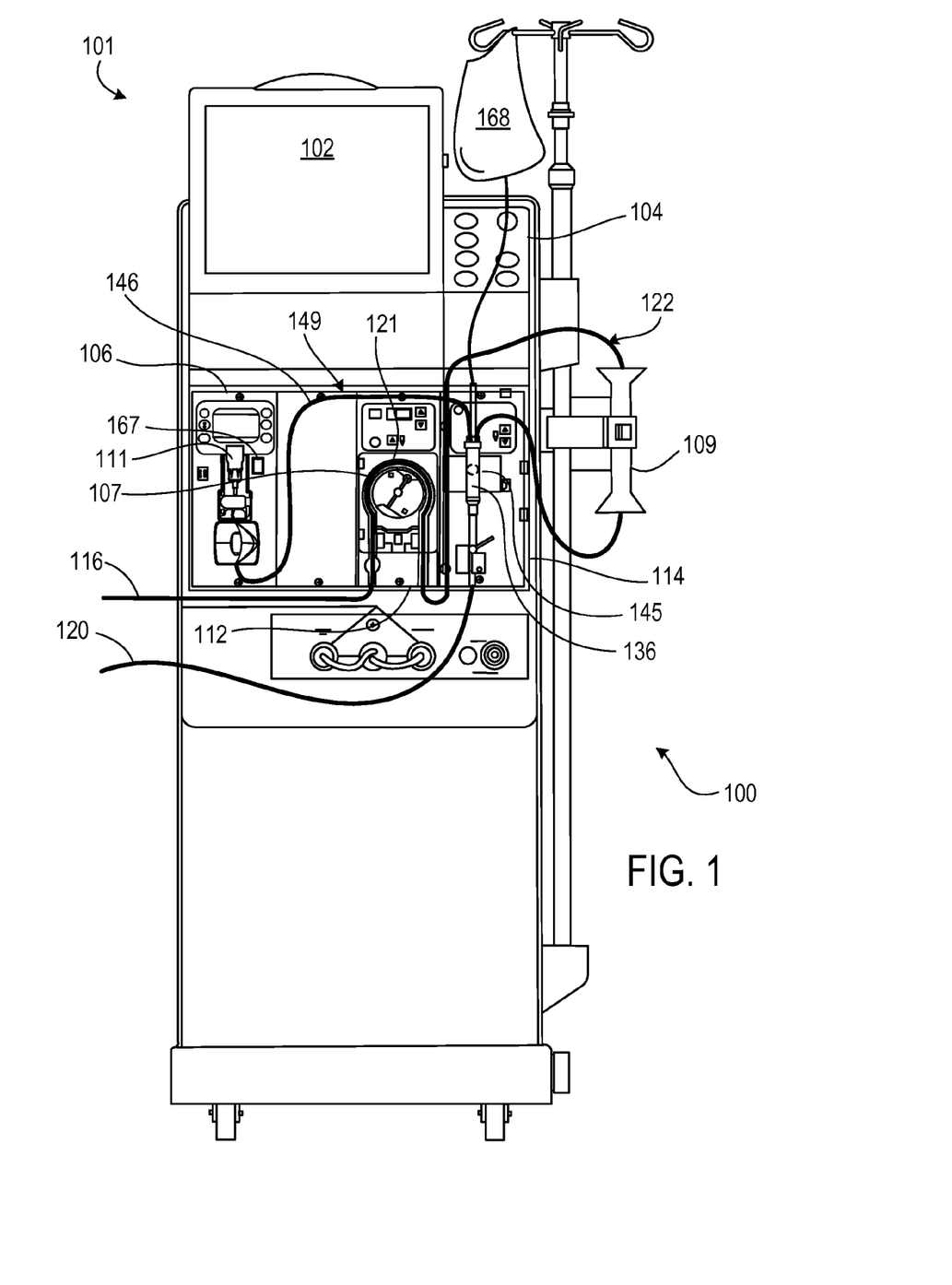
FIG. 1 is a front view of a hemodialysis machine including a drug delivery module mounted in a mid-section of the machine.

Referring to FIG. 1, a hemodialysis system 101 includes a hemodialysis machine 100 having a drug delivery module 106 to which a drug delivery line set 149 is connected. The drug delivery module 106 and drug delivery line set 149 can be used to deliver drugs to a patient during hemodialysis treatment. Specifically, the drugs can be delivered from a drug vial 111 through the drug delivery line set 149 to a drip chamber 136 of a blood line set 122 where the drug mixes with blood before the blood is returned to the patient. The drug delivery line set 149 can be primed with a priming fluid (e.g., saline from a priming fluid bag 168) prior to drug delivery. As will be described in detail below, a spike cover 138 (shown in FIGS. 3-6) of the drug delivery line set 149 includes an indicator material that changes color when contacted by the priming fluid and indicates to the user that the drug delivery line set 149 has been successfully primed. This color change is monitored by a color change sensor 167 positioned on the drug delivery module 106 adjacent to the spike cover 138. When priming is complete, the hemodialysis system 101 is ready for use with a patient.

Still referring to FIG. 1, the hemodialysis machine 100 includes a display 102 and a control panel 104, whereby the user selections and instructions can be sent to, and stored by, a control unit of the hemodialysis machine 100. The hemodialysis machine 100 also includes modules that house components used to perform hemodialysis, including the drug delivery module 106, a blood pump module 112, and a level detector module 114.

In use, the disposable blood line set 122, which forms a blood circuit, is connected to the modules 106, 112, and 114 on the front side of the hemodialysis machine 100. During treatment, patient lines 116, 120 of the blood line set 122 are connected to the patient and a pump tubing segment 121 of the blood line set 122 is connected to a blood pump 107 of the blood pump module 112. As the blood pump 107 is operated, blood is drawn from the patient, pumped through a dialyzer 109 and the drip chamber 136 of the blood line set 122, and then returned to the patient.

Figure 2:
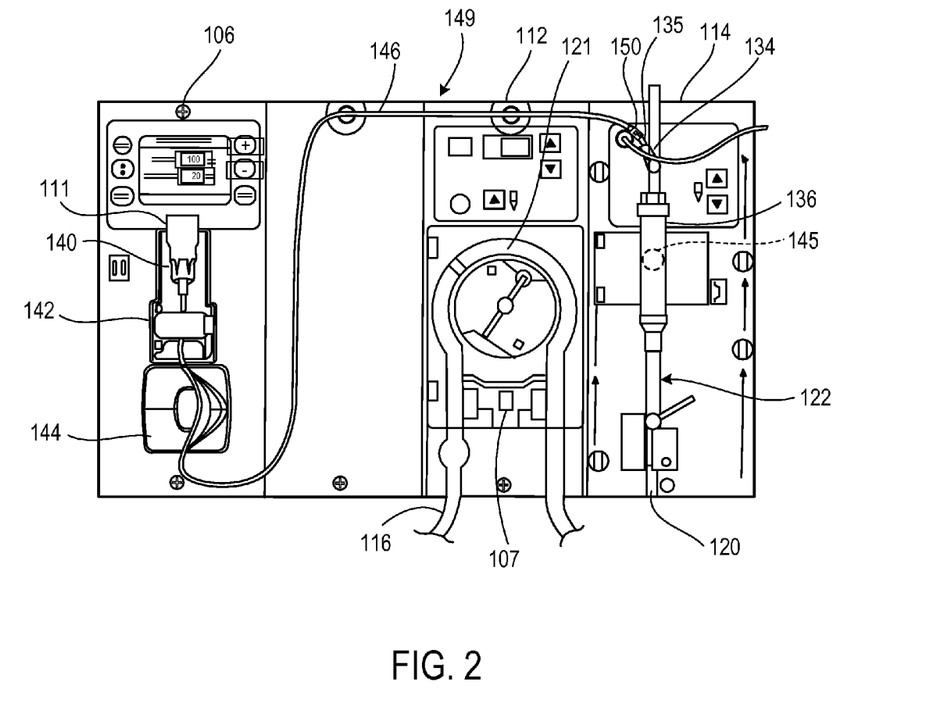
FIG. 2 is an enlarged view of the midsection of the hemodialysis machine of FIG. 1.

FIG. 2 illustrates the mid-section of the hemodialysis machine 100 with the blood line set 122 and the drug delivery line set 149 connected to the modules 106, 112, and 114 and with a drug vial 111 inserted into a vial adapter 140 of the drug delivery line set 149. The blood line set 122 includes the pump tubing segment 121, which is connected to the blood pump module 112 in a manner so as to operatively engage the blood pump 107 of the blood pump module 112. Operation of the blood pump 107 pumps blood through the blood line set 122.

Still referring to FIG. 2, the drip chamber 136 of the blood line set 122 is positioned at a location downstream from the blood pump 107. The drip chamber 136 permits gas, such as air, in the blood to escape from the blood before the blood is returned to a patient. The drip chamber 136 can be secured to the level detector module 114 so as to align with a fluid level detector 145 that is adapted to detect the level of liquid (e.g., blood and/or saline) within the drip chamber 136. A drug delivery line 146 of the drug delivery line set 149 is connected via a luer lock connector 150 to the blood line set 122 at a location between the dialyzer 109 and the drip chamber 136. Specifically, the luer lock connector 150 is connected to a mating luer locking fitting on a level adjust line 135 that is connected to the top of the drip camber 136. A clamp 134 is attached to the level adjust line 135 and is used to permit or block fluid from passing between the drug delivery line set 149 and the blood line set 122.

Figure 3:
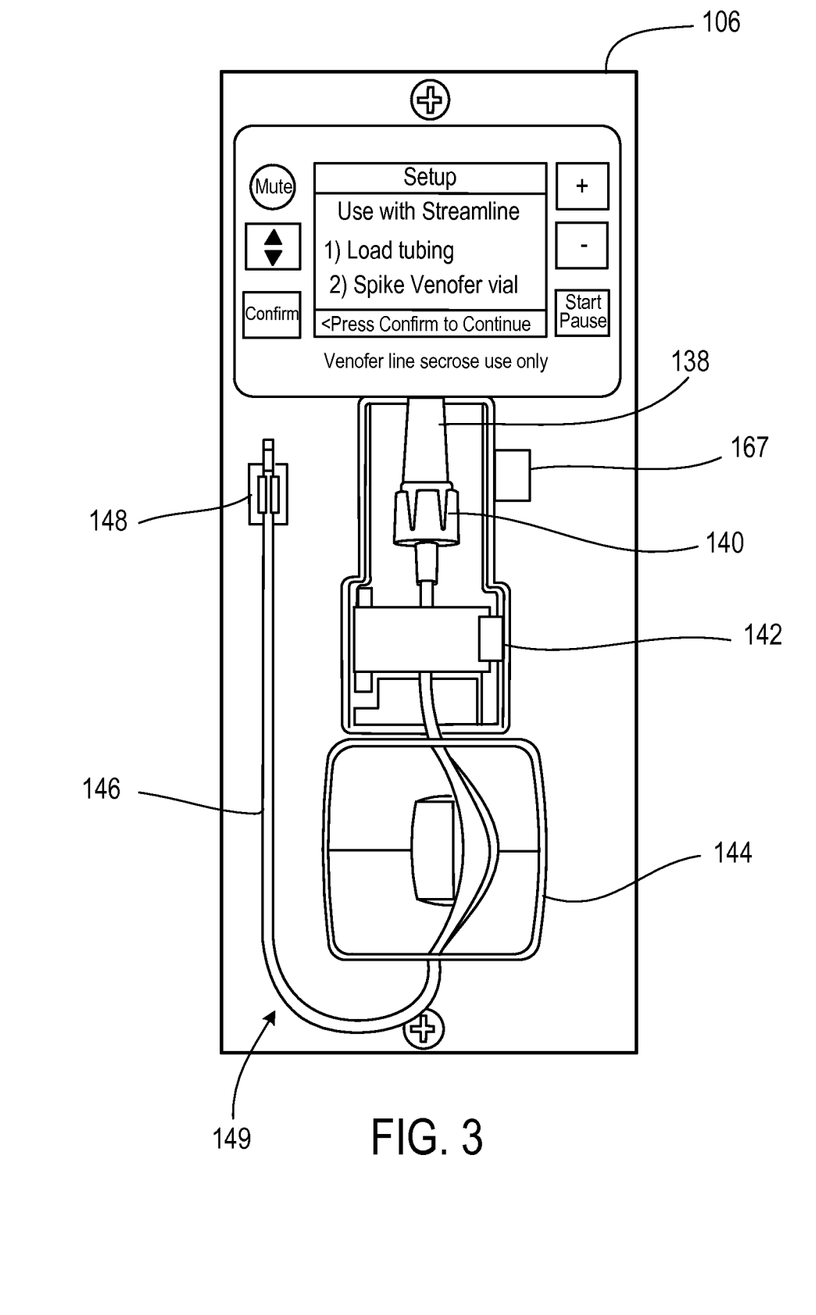
FIG. 3 is an enlarged view of the drug delivery module of the hemodialysis machine of FIG. 1 isolated from the hemodialysis machine.

FIG. 3 shows the drug delivery line set 149 connected to the drug delivery module 106 prior to connecting the drug delivery line 146 to the blood line set 122. As shown, the end of the drug delivery line 146 is connected to a storage clip 148 of the drug delivery module 106. The drug delivery line 146 passes through a peristaltic drug pump 144. Prior to use, a user would unclip the drug delivery line 146 from the storage clip 148 and connect it to the blood line set 122 in the manner shown in FIGS. 1 and 2.

Still referring to FIG. 3, the drug delivery module 106 also includes the color change sensor 167 and a fluid flow detector 142. The color change sensor 167 is adjacent to the spike cover 138 and generates a signal and transmits the signal to a control unit (e.g., a processor) of the dialysis machine 100. Based on the received signal, the control unit can activate an indicator (e.g., an audible or visual device that indicates a color change has occurred) to signal the completion of the priming cycle. In some examples, the color change sensor 167 is an optical sensor.

The fluid flow detector 142 is capable of detecting air bubbles within the drug delivery line 146. As a result, the fluid flow detector 142 can determine whether the drug vial 111 is empty. In some implementations, the fluid flow detector 142 is an optical detector. The OPB 350 level detector made by Optek® can, for example, be used. Other types of optical detectors can alternatively or additionally be used. Similarly, other types of sensors, such as sensors utilizing ultrasound technology can be used as the fluid flow detector. Examples of such sensors include the AD8/AD9 Integral Ultrasonic Air-In-Line, Air Bubble Detector and the BD8/BD9 Integral Ultrasonic Air Bubble, Air-In-Line & Liquid Level Detection Sensors (manufactured by Introtek® International (Edgewood, N.Y.)). In some implementations, the fluid flow detector 142 includes a sensor that, in addition to sensing the presence of an air bubble within its associated drug delivery line 146, can sense the presence of the drug delivery line 146 itself.

Still referring to FIG. 3, the drug delivery line 146 passes through (e.g., is threaded through) the peristaltic drug pump 144. The peristaltic drug pump 144 works by compressing the drug delivery line 146 and moving a "pillow" of fluid that is pinched between two points of the drug delivery line 146 by the pump rollers. Each "pillow" of fluid is of a volume determined by the roller spacing and the inside diameter of the drug delivery line 146. When the peristaltic drug pump 144 operates at a given speed, a series of these "pillow" shaped volumes of fluid are delivered to the drip chamber 136. The rate of fluid delivery can be changed by altering the speed of the peristaltic drug pump 144. The pump speed can be controlled, for example, by adjusting the voltage delivered to the peristaltic drug pump 144. The voltage delivered to the motor of the peristaltic drug pump 144 can, for example, be adjusted by the control unit (e.g., software of the control unit) until the correct speed (e.g., the speed that corresponds to the desired flow rate) is measured by an encoder of the peristaltic drug pump 144.

During use, the drug delivery line set 149 is fluidly connected to the blood circuit 122 of the hemodialysis system 101, as shown in FIGS. 1 and 2. Drugs are delivered to the drip chamber 136 using the drug delivery module 106. The drugs mix with the patient's blood within the drip chamber 136 and are then delivered to the patient along with the patient's filtered blood.

Figure 4:
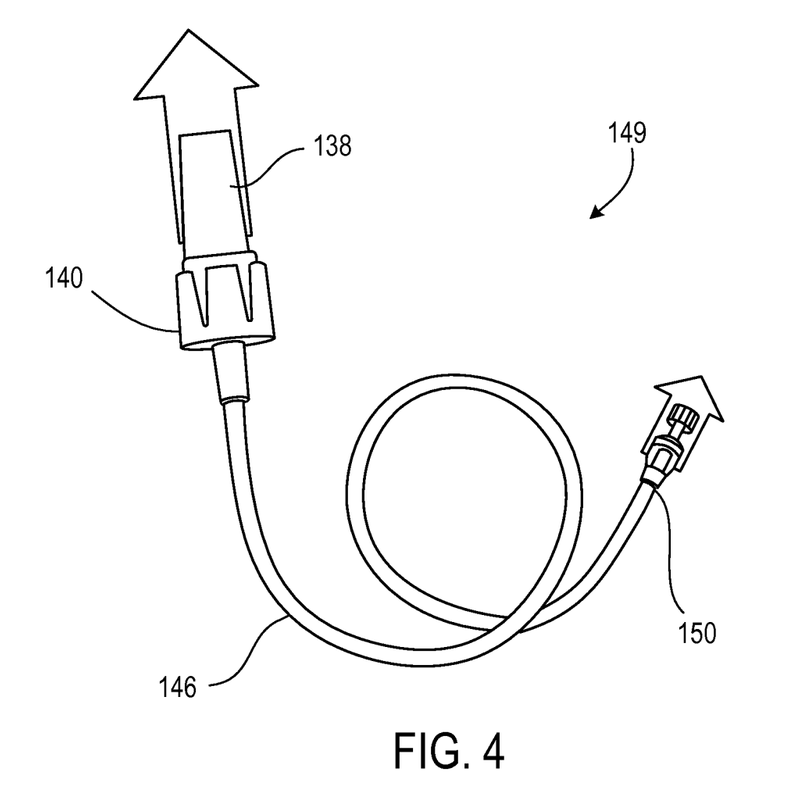
FIG. 4 is a perspective view of a drug delivery fluid set including a vial spiking assembly connected to a drug delivery line.

Referring to both FIGS. 3 and 4, the drug delivery line set 149 includes the vial adapter 140 to which the drug delivery line 146 is attached. The spike cover 138 is removably secured to the vial adapter 140 by an interference fit. The spike cover 138 is removed from the vial adapter 140 prior to use to allow a drug vial (e.g., the drug vial 111) to be inserted into the vial adapter 140.

Figure 5:
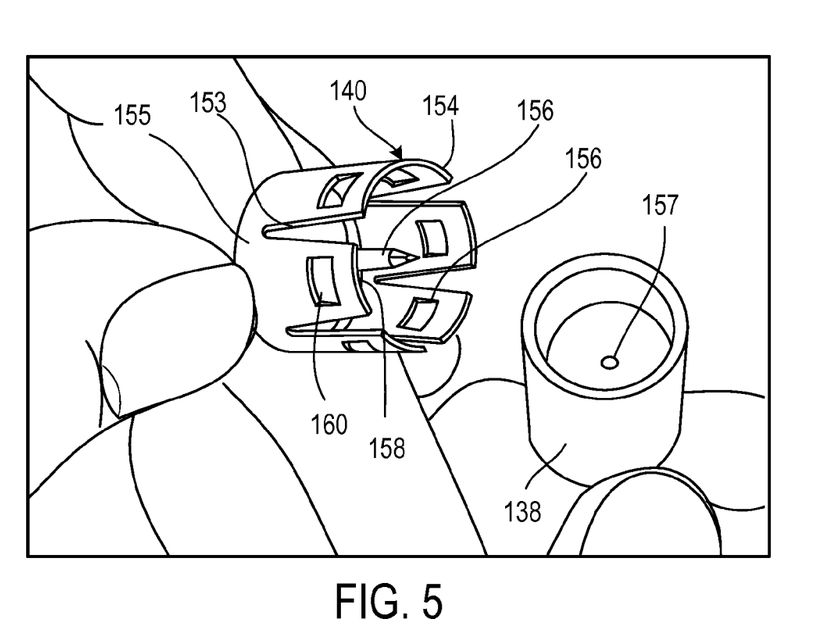
FIG. 5 is a perspective view of the vial spiking assembly of FIG. 4 including a vial adapter and a spike cover that can be disposed over a spike of the vial adapter.

FIG. 5 illustrates the vial adapter assembly with the spike cover 138 removed from the vial adapter 140. The vial adapter 140 includes circumferentially spaced side wall segments 154 that extend upwardly from a base 155 to form a receiving cavity 158 sized and shaped to receive a drug vial. A spike 156 extends from a central region of the base 155 and is sized and shaped to pierce a seal of the drug vial when the drug vial is inserted into the receiving cavity 158. The spike 156 has a central passage in fluid communication with a cavity 157 of the spike cover 138 when the spike cover 138 is positioned over the spike 156.

As shown in FIG. 5, the circumferential side wall segments 154 of the vial adapter 140 extend to a slightly greater height than the spike 156 of the vial adapter 140. Adjacent side wall segments 154 are spaced apart by longitudinal/vertical slots 153. The side wall segments 154 together with the base 155 form the receiving cavity 158 that is configured to receive a portion of a drug vial (e.g., a collar of a drug vial cap assembly). In some implementations, the receiving cavity 158 is configured to receive a collar having a diameter that is about 0.75 inches to about 1 inch (e.g., about 0.875 inches.) The side wall segments 154 are configured to deflect away from the longitudinal axis of the vial adapter 140 when a radially outward force is applied (e.g., as a result of the drug vial being inserted into the receiving cavity 158) and rebound towards the longitudinal axis when the force is released.

Still referring to FIG. 5, protrusions 160 on side wall segments 154 of the vial adapter 140 help secure a vial within the receiving cavity 158 of the vial adapter 140. The extension of the side wall segments 154 to a slightly greater height that the spike 156 of the vial adapter 140 also help to ensure that the spike 156 is not inadvertently contacted (e.g., by the user) prior to loading of the drug vial 111 onto the spike 156. This can, for example, help to prevent the spike 156 from becoming contaminated before it is inserted into the drug vial.

In some implementations, the spike 156 is formed of one or more medical grade plastics, such as PVC or acrylonitrile butadiene styrene (ABS). However, other medical grade plastics can be used to form the spike 156. Similarly, certain metals, such as stainless steel, could be used to form the drug vial spike 156.

Another feature of the vial adapter assembly that prevents inadvertent contact and contamination is the spike cover 138. The spike cover 138 is placed into the receiving cavity 158 of the vial adapter 140 to cover the spike 156. The spike cover 138 can help prevent objects from contacting and contaminating the spike 156 prior to use and can also prevent users from inadvertently sticking themselves with the spike 156. The spike cover 138 is configured to be received in the receiving cavity 158 and temporarily retained by the side wall segments 154. For example, the spike cover 138 can be retained via a loose interference fit. The side wall segments 154 provide a resisting force of about 0.75 lbf to about 2 lbf to retain the spike cover 138 when it is retained by the vial adapter 140.

Figure 6:
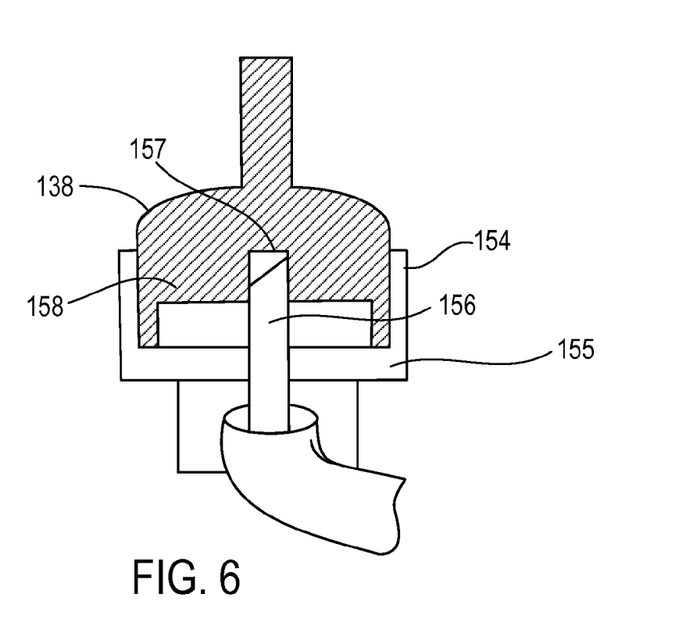
FIG. 6 is a cross sectional of the vial spike assembly of FIG. 4 with the spike cover secured to the vial adapter.

As shown in FIG. 6, the base 155 of the vial adapter 140 is solid. To allow air to vent out of the vial adapter assembly, the spike cover 138 is gas permeable and fluid impermeable. The spike cover 138 is made out of a microporous material (e.g., Polyethylene or high density Polyethylene) having a porosity of about 7 microns (e.g, 5 to about 45 microns). The microporous material of the spike cover 138 can withstand sufficient water intrusion pressure so as not to leak fluid, but is sufficiently porous to be gas permeable. In certain implementations, this water intrusion pressure is about 200 mbar (2.90 psi) over ¼ inch material thickness (i.e., the radial distance from the spike to the outer diameter of the cover). The spike cover 138 can be molded (e.g., using heat and/or pressure) or milled to the appropriate dimensions. The spike cover 138 forms the cavity 157, which is sized to create a seal between the cavity 157 and the spike 156 of the vial adapter 140 (e.g., by radial interference fit). The cavity 157 is also slightly longer than the exposed position of the spike 156 so that the tip of spike 156 is not damaged during use (e.g., when the spike cover is attached). The spike cover 138 is removably attached to the vial adapter 140 by an interference fit capable of resisting force generated by the priming system. The combination of the retaining strength of the vial adapter 140 and the sizing of the cavity 157 forms a seal that prevents leaking at the interface between the spike cover 138 and the vial adaptor 140.

As shown in FIG. 6, when the spike cover 138 is disposed in the receiving cavity 158 of the vial adapter 140, the microporous material of the spike cover 138 surrounds the spike 156. The microporous material inhibits the flow of liquid while allowing gases (e.g., air) to pass there through. During manufacture, the microporous material of spike cover 138 is impregnated with color changing additives. For example, the color changing additives can be incorporated during molding and/or surface coated. These additives are liquid sensitive and exhibit a physical change, e.g., change color, when they are contacted by liquid. This color change is visible through the microporous material of the spike cover 138. Examples of color changing additives that can be used include bromophenol blue, cobalt chloride, and food dye in powder or granular form. Other liquid triggered color changing materials are known in the art. These additives may also be used to create a film or liquid that is applied over, or covalently bonded to, the microporous material of the spike cover 138.

Methods of Use

Prior to hemodialysis, the user connects the drug delivery line set 149, which includes the vial adapter 140, the spike cover 138, and the drug delivery line 146, to the drug delivery module 106 of the dialysis machine 100. The drug delivery line set 149 is typically provided to the user in a sterile bag. To connect the drug delivery line set 149 to the drug delivery module 106, the user first opens the sterile bag and removes the drug delivery set 149.

Figure 7:
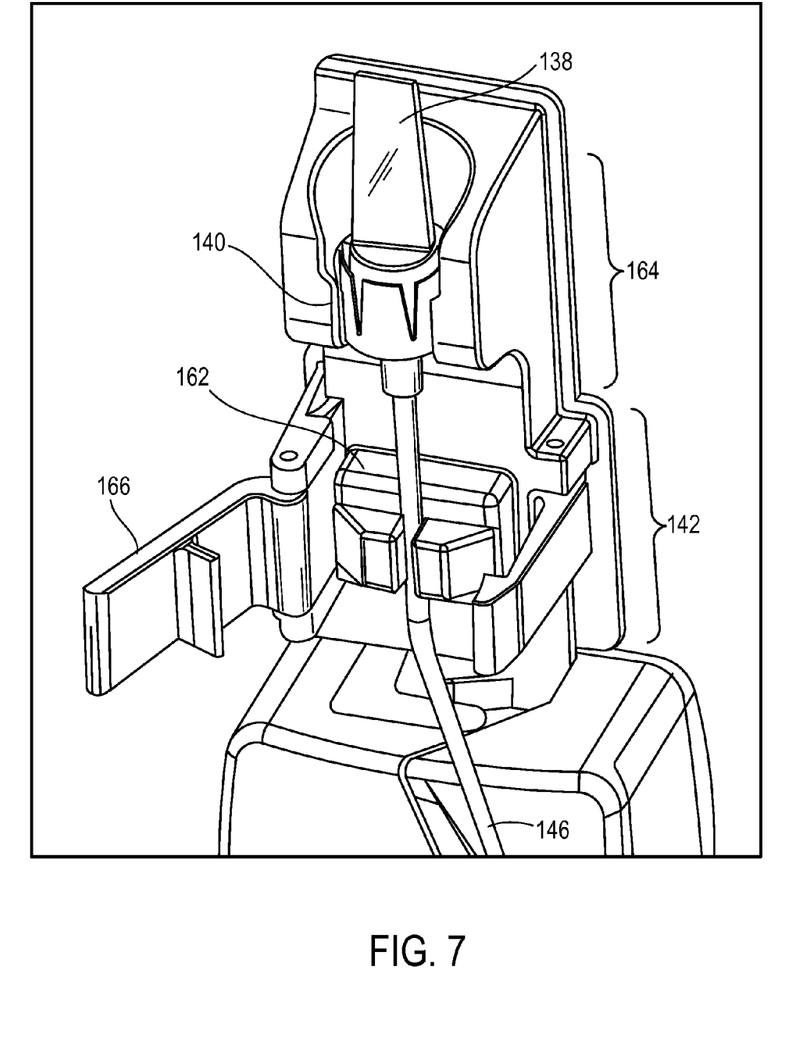
FIG. 7 is a perspective view of the drug delivery line set partially loaded into the drug delivery module.

Referring to FIG. 7, the user then opens a door 166 of the fluid flow detector 142, places vial adapter assembly (e.g., the vial adapter 140 and spike cover 138) into a vial holder 164, and threads the drug delivery line 146 through a fluid flow sensor 162 of the fluid flow detector 142.

Figure 8:
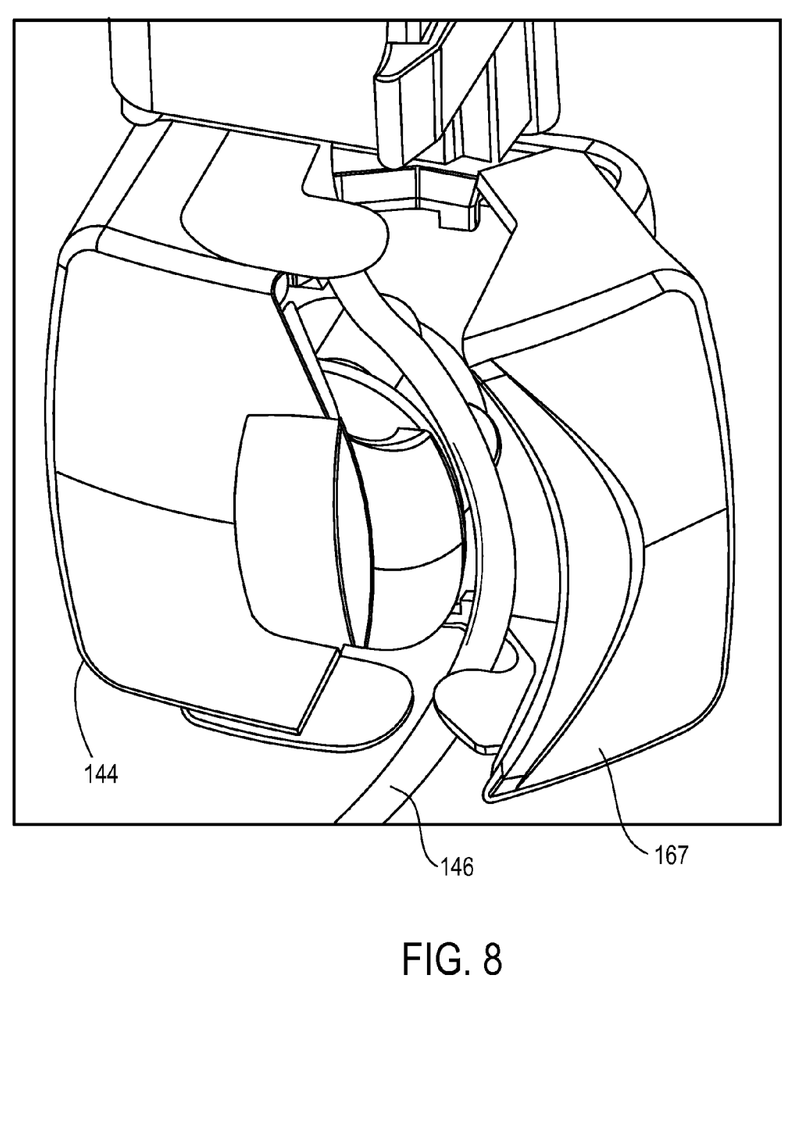
FIG. 8 is a perspective view of the drug delivery line set being loaded into a peristaltic pump of the drug delivery module.

Referring to FIG. 8, the user then opens a door 167 of the peristaltic drug pump 144 and threads the drug delivery line 146 through the peristaltic drug pump 144. The door 167 remains open so that the drug delivery line 146 is not crimped between the door 167 and rollers of the drug pump 144. This permits fluid to flow freely through the drug delivery line 146.

Figure 9:
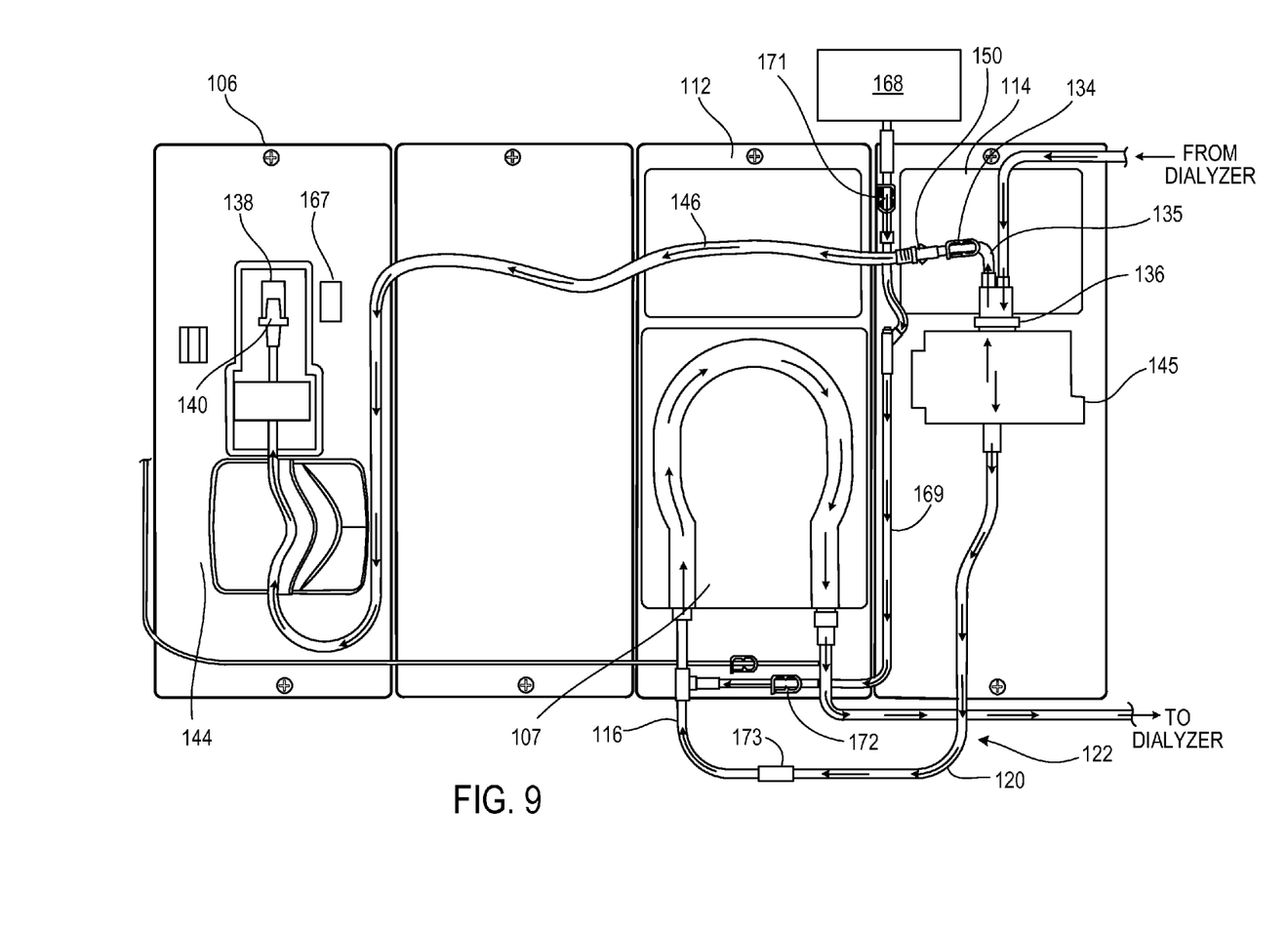
FIG. 9 is an enlarged view of the midsection of the hemodialysis machine of FIG. 1 during priming, showing priming fluid flowing through the drip chamber and drug delivery line set to the spike cover.

Referring to FIG. 9, the drug delivery line 146 is then connected to the drip chamber 136 using an aseptic technique. As discussed above, this typically involves connecting the luer lock fitting 150 on an end of the drug delivery line 146 to a mating luer lock fitting on the level adjust line 135 extending from the drip chamber 136. However, other types of connectors can be used. In addition, the priming fluid bag 168 is connected to the blood line set 122 via a priming fluid line 169. The priming fluid bag 168 is connected to the priming fluid line 169 by a luer lock connection. The priming fluid line 169 also includes clamps 171 and 172 that are used to regulate the fluid flow from the fluid bag 168 to the blood line set 122.

Still referring to FIG. 9, after the drug delivery line set 149 has been connected to the drip chamber 136, which is attached to the level detector module 114, the patient lines 116 and 120 are connected by a luer connector 173 so as to form a closed circuit. The drug delivery line set 149 is now ready to be primed. The clamps 171 and 173 are released and gravity draws priming fluid (e.g., saline) from the fluid bag 168. The blood pump 107 then pumps the priming fluid through the blood line set 122 to the dialyzer 109 and then from the dialyzer 109 to the drip chamber 136. The blood pump 107 pumps the priming fluid at a sufficient rate (e.g., 100-300 mL/min) to overfill the drip chamber 136, despite a portion of the priming fluid continuing through line 120. The overfilling of the drip chamber 136 generates back pressure that causes the priming fluid to travel through the drug delivery line 146 towards the spike cover 138.

Figure 10:
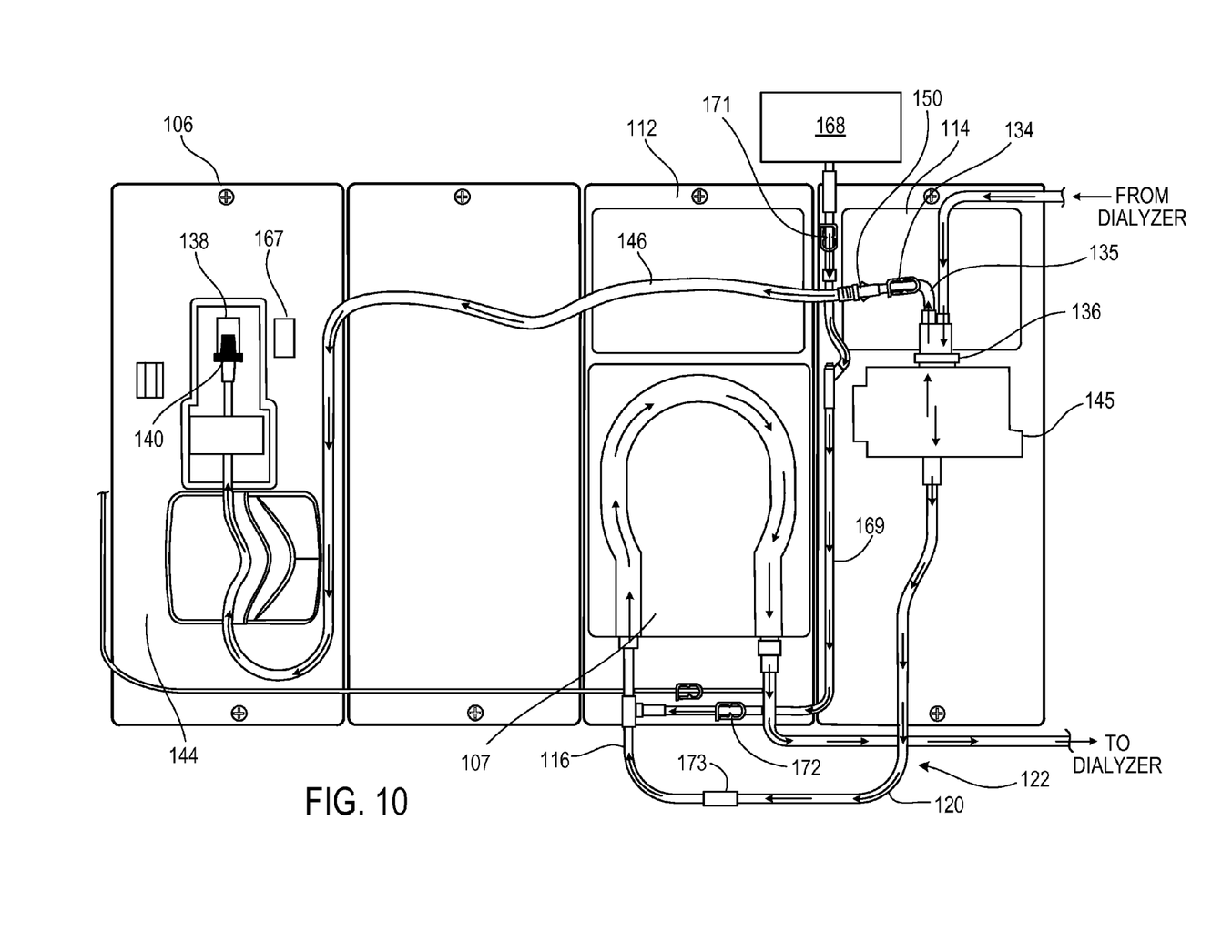
FIG. 10 is an enlarged view of the midsection of the hemodialysis machine of FIG. 1 in which priming fluid has reached the spike cover of the vial spiking assembly causing a microporous membrane within the spike cover to change color.

Referring to FIG. 10, the priming fluid flows from the drip chamber 136 toward the spike cover 138 of the vial adapter 140 via the drug delivery line 146. Once the priming fluid travels through the spike 156 (shown in FIGS. 5 and 6) of the vial adapter 140, the priming fluid contacts the microporous material of the spike cover 138. As the priming fluid travels through the drug delivery line 146 to the vial adapter 140 any air remaining in the drug delivery line 146 is forced towards the drug vial adapter assembly and eventually out of the spike tip. The microporous spike cover material permits air to pass through the spike cover 138 while retaining the priming fluid within the system. Thus, after the air exits the spike tip, it passes through the microporous material of the spike cover 138 to the surrounding environment. This helps to ensure that no air is trapped within the system and thus helps to ensure efficient delivery of drug from the drug vial 111. Priming the drug delivery line set 149 in this way can also protect the ingress of pathogens via the vial adapter 140.

After the air from the drug delivery line set 149 has exited the vial adapter 140 and drug delivery line 146, the priming liquid also exits the spike 156 of the vial adapter 140. The priming fluid then comes into contact with the color changing indicator material impregnated in the microporous material of the spike cover 138. A change in color of this indicator material indicates to the user that the priming cycle is complete, with respect to the drug delivery module 106. The sensor 167 adjacent to the spike cover 138 detects the color change and generates a signal when the priming cycle is complete. The signal is transmitted to the control unit and causes the control unit to activate an audible or visual indicator (e.g., using the display 102) to indicate the completion of the priming cycle.

After priming the lines, the clamps 171 and 172 are closed and the patient lines 116 and 120 are also clamped. The connection between the patient lines 116 and 120 is also severed in anticipation of connection to a patient. The door 167 of the peristaltic drug pump 144 is closed, and the spike cover 138 is removed. The drug vial 111 is placed on the vial adapter 140 so that the spike 156 pierces a seal of the drug vial 111 and places the vial in fluid connection with the drug delivery line set 149 (e.g., as shown in FIGS. 1 and 2). The peristaltic drug pump 144 is then operated to deliver drug to the drip chamber 136 of the blood line set 122. The volume of drug delivered to the patient is monitored and controlled by the control unit and the peristaltic drug pump 144 of the drug delivery device 106.

As discussed above, the drip chamber 136 of the hemodialysis system 101 functions as an air trap. Thus, any gases (e.g., air) introduced into the system are able to escape from the drug and blood within the drip chamber 136 before the mixture of blood and drug is delivered to the patient. In addition to removing air from the system, the drip chamber 136 provides other benefits. For example, the drip chamber 136 provides visual confirmation of drug delivery and allows the delivered drug to mix with the patient's blood prior to reaching the patient. In addition, the drip chamber 136 allows for simple luer connection to the drug delivery line set 149. As a result, the patient need not be stuck with an additional needle in order to receive the drug from the drug vial 111.

Alternative Implementations

While the sidewall portions of the vial adapter 140 are generally shown to be vertical to the base of the vial adapter and having a height exceeding that of the spike, other configurations are possible. For example, the vial adapter may have fingers and side wall segments that project at a non-perpendicular angle from the base of the vial adapter so as to generate resisting forces as the vial is inserted into the vial adapter. The vial adapter may further include sidewalls that have a height that is less than that of the spike.

While the base of the vial adapter is generally shown as being solid, other configurations are possible. For example, the base of the vial adapter may have one or more (e.g., 1, 2, 3, 4, 5, 6, 7, and 8) holes arranged around the spike. These one or more holes permit a fluid and/or air to flow in and out of the vial adapter. The material of the spike cover may be selected based on the presence and/or number of ventilation holes. For example, in examples where the vial adapter contains ventilation holes, the vial adapter can be provided with a gas impermeable spike cover since gasses are allowed to vent to the atmosphere via the ventilation holes and need not pass through the spike cover. In some implementations, the number of holes correlates with the number of wall segments arranged around the base, and the holes are typically aligned with the wall segments.

While the spike cover has been described as including a color changing material, in certain implementations, at least some portions of the vial adapter, e.g., the base, the drug delivery line, and/or the spike, can alternatively or additionally include a color changing material that changes color when the portions are exposed to a liquid. For example, the base, the drug delivery line, and/or the spike can include a coating impregnated with a color changing material. The base, the drug delivery line, and/or the spike can be made from a transparent or semi-transparent material so that when the coating undergoes a color change, the color change is visible to the user.

While the vial adapter is generally shown to include six sidewall segments, more, or fewer sidewall segments are possible. For example, in some implementations, the sidewall of the vial adapter includes two, three, four, five, or more sidewall segments. Alternatively, the sidewall of the vial adapter includes only one continuous sidewall segment.

While the sidewall segments are generally shown to have protrusions to help secure the spike cover and/or vial within the assembly, other securing means are possible. For example the sidewalls may not significantly deform when the spike cover and/or drug vial is inserted into or removed from the vial adapter. While the sidewall segments provide a force to retain the spike cover and/or drug vial, they do not lockingly engage any mating features of the spike cover and/or drug vial. As a result, the spike cover and/or drug vial can be removed without damaging or altering the vial adapter.

While the vial and vial adapter devices have been described as having a generally circular cross-section, other shaped vials and/or vial spiking mechanisms are possible. For example, the vial and/or the vial spiking device, in particular, the interface between the vial and the drug vial spiking device, can have other cross-sectional shapes, such as an ellipse, a polygon (e.g., a rectangle, a square, a pentagon, a hexagon, or another polygon), or other structurally suitable shapes.

While some of the drug vial assemblies have been shown as being substantially integral one-piece components, other configurations are possible. For example, one or more portions of the drug vial devices (e.g., the base, the spike, the sidewall segments, and/or the fingers) can be formed as separate components that can be attached to one another to form the drug vial spiking device.

While the spike of the vial adaptor has been described as being uncoated, in some implementations, a tip region of the spike includes a silicone coating. Such a coating can reduce friction associated with initially piercing the seal of the vial with the spike. Any of various techniques can be used to apply the silicone coating to the tip region of the spike. In certain cases, for example, a dip coating technique is used to coat the tip region of the spike.

While the spike cover has been described as using a polyethylene (PE) material, in some implementations other materials can be used. For example, in some implementations, the microporous material is polyethylene (e.g., high density polyethylene (HDPE)) and carboxymethylcellulose (CMC), a blend of polystyrene and methyl-ethyl-cellulose or of polypropylene- or polyethylene-based porous material. It can include about 80% to about 95% by weight high density polyethylene and about 5% to about 20% by weight carboxymethylcellulose.

While the spike cover is generally described as a microporous material including a color changing material, in some implementations a microporous material is inserted into a housing of the spike cover. For example, a microporous material may be modified by adding high density polyethylene powder, carboxymethyl cellulose powder, cobalt chloride, and/or a powder dye, in the desired proportions into a mold and applying heat and pressure to the mixture to form a solid porous block which takes the shape of the mold and can be later fitted into a separate spike cover. This microporous block may be fitted into a recess and attached to the spike cover by an interference fit and/or an adhesive connection.

While the drug delivery module generally shown includes a sensor adjacent to the spike cover that indicates a color change has occurred, visual confirmation by an user and/or user of the hemodialysis machine may be used in place of or in addition to such a sensor. The hemodialysis machine may also include a user interface configure to guide the user through the priming process by displaying a series of messages and/or graphics. For example, the control module may generate and provide the user with a graphic of an unwetted spike cover on the display. This graphic may also include messages directing the user to activate the priming cycle. After a predetermined period of time, the display may show a new graphic including a wetted spike cover along with user instructions to end the priming cycle after the spike cover matches the graphic. The control module may further prompt the user, via the display or any audible means, to remove the spike cover and insert a drug vial. The control module may continue to provide user instructions throughout the hemodialysis priming or treatment.

While the priming technique generally shown includes generating backpressure in the drip chamber thus diverting fluid through the drug delivery line, other methods of priming are possible. For example, the drug delivery line may be connected directly to a portion of the bloodline distal to the blood pump but before the drip chamber. This connection may allow the blood pump to directly prime the drug delivery line.

While the drug delivery line is generally shown as connected to the hemodialysis system before priming, other methods of priming are possible. For example, a syringe may be connected to the drug delivery line, and priming fluid may be delivered manually until the fluid line is primed and the spike cover indicator has indicated fluid contact, e.g., changed color, shape, and/or size.

While during priming the drug delivery line is generally shown as threaded through the peristaltic drug pump, the drug delivery line may remain outside of the peristaltic pump until priming is complete.

While the hemodialysis machine has generally been shown to include modules used to perform hemodialysis, including the drug delivery module, the blood pump module, and the level detector module, other modules may also be included. For example, a heparin pump module may also be included. The heparin pump module can include a heparin pump that receives a syringe connected to a drug delivery line that is connected to the blood line at a location between the blood pump. The syringe pump can be operated to move a plunger of the syringe and thus eject liquid from the syringe through the drug delivery line. The heparin pump module can thus be used to inject heparin from the syringe into the blood circuit via the drug delivery line during a hemodialysis treatment.

While the drug delivery devices have been described as being used with hemodialysis systems, the devices, assemblies, and methods described herein can be used with various other types of drug delivery processes and systems. For example, in some implementations, the drug vial spiking devices are used for delivering drugs during peritoneal dialysis treatments, blood perfusion treatments, intravenous infusion treatments, or other medical fluid handling treatments, such as delivering drugs intravenously.

A number of implementations have been described. Nevertheless, it will be understood that various modifications may be made without departing from the spirit and scope of the description. Accordingly, other implementations are within the scope of the following claims.

What is claimed is:

1. A vial spiking assembly comprising:
   a vial adapter comprising:
   a base;
   a spike extending from a central region of the base; and
   a sidewall extending from the base and substantially surrounding the spike, the base and the side wall at least partially defining a cavity configured to receive a portion of a vial; and
   a spike cover removably attachable to the spike, wherein the spike cover comprises a microporous material configured to indicate when the material has been contacted with liquid, wherein the microporous material has an average pore size capable of permitting air to flow therethrough and preventing liquid from flowing therethrough.

2. The assembly of claim 1, wherein the microporous material is a color changing material that changes color when contacted by a liquid.

3. The assembly of claim 2, wherein the color changing material is a microporous material impregnated with at least one of the following: bromophenol blue, cobalt chloride, a food dye, powder dye, and a color additive.

4. The assembly of claim 1, wherein the microporous material is molded with a color additive that changes color when contacted with liquid.

5. The assembly of claim 1, wherein the microporous material surrounds the spike when the spike cover is attached to the spike.

6. The assembly of claim 1, wherein the spike cover is movable away from the base from a first position wherein the cover at least partially covers a tip of the spike of the vial adapter to a second position wherein the tip of the vial adapter is fully exposed.

7. The assembly of claim 1, wherein the spike cover comprises a housing defining a cavity in which the microporous material is disposed.

8. The assembly of claim 7, wherein the housing is formed of a gas permeable material.

9. The assembly of claim 7, wherein the microporous material is visible through the housing.

10. A dialysis system comprising:
    a dialysis machine comprising:
    a blood pump; and
    a drug pump;
    a blood line set comprising a blood line that can be operably connected to the blood pump and a drip chamber in fluid communication with the blood line; and
    a fluid line set comprising a fluid line that can be connected to the drip chamber of the blood line set and to a vial adapter, the vial adapter comprising:
    a base;
    a spike extending from a central region of the base; and
    a sidewall extending from the base and substantially surrounding the spike, the base and the side wall at least partially defining a cavity configured to receive a portion of a vial; and
    a spike cover removably attachable to the spike, wherein the spike cover comprises a microporous material configured to indicate when the material has been contacted with liquid, wherein the microporous material has an average pore size capable of permitting air to flow through and preventing liquid from flowing through.

11. The dialysis system of claim 10, wherein the microporous material is a color changing material that changes color when contacted by a liquid.

12. The dialysis system of claim 10, wherein the drip chamber is downstream of the blood pump and the fluid line is connected to a top region of the drip chamber.

13. The dialysis system of claim 11, wherein the color changing material is a microporous material impregnated with at least one of the following: bromophenol blue, cobalt chloride, a food dye, powder dye, and a color additive.

14. The dialysis system of claim 11, wherein the microporous material is covalently bonded with a color additive that changes color when contacted with liquid.

15. The dialysis system of claim 10, wherein the microporous material surrounds the spike when the spike cover is attached to the spike.

16. The dialysis system of claim 10, wherein the spike cover comprises a housing defining a cavity in which the microporous material is disposed.

17. The dialysis system of claim 16, wherein the housing is formed of a gas permeable material.

18. The dialysis system of claim 16, wherein the microporous material is visible through the housing.

19. The dialysis system of claim 10, wherein the drip chamber is downstream of the blood plump.

20. The dialysis system of claim 10, wherein the fluid line is connected to a top portion of the drip chamber.

21. The dialysis system of claim 10, wherein the dialysis machine is configured to pump priming fluid through the fluid line set toward the vial adapter until the priming fluid contacts the microporous material.

22. The dialysis system of claim 10, wherein the dialysis machine is configured to pump priming fluid through the blood line set in a manner to overfill the drip chamber and cause the priming fluid to flow through the fluid line set toward the vial adapter, until the priming fluid contacts the microporous material.

23. The vial spiking assembly of claim 1, wherein the microporous material forms an exterior of the spike cover.

24. The dialysis system of claim 10, wherein the microporous material forms an exterior of the spike cover.

\* \* \* \* \*

UNITED STATES PATENT AND TRADEMARK OFFICE
CERTIFICATE OF CORRECTION

PATENT NO.        : 9,433,721 B2
APPLICATION NO.   : 13/926500
DATED             : September 6, 2016
INVENTOR(S)       : Nigel Wright et al.

Page 1 of 1

It is certified that error appears in the above-identified patent and that said Letters Patent is hereby corrected as shown below:

In the claims

In Column 12, line 53, in Claim 14, delete "The dialysis system of claim 11" and insert --The dialysis system of claim 10--, therefor.

Signed and Sealed this
Thirteenth Day of December, 2016

Michelle K. Lee
*Director of the United States Patent and Trademark Office*